(12) United States Patent
Inoue et al.

(10) Patent No.: US 9,226,703 B2
(45) Date of Patent: Jan. 5, 2016

(54) HOLDER AND LIGHT MEASUREMENT DEVICE EMPLOYING SAME

(75) Inventors: Yoshihiro Inoue, Kyoto (JP); Takashi Amita, Kyoto (JP); Satoru Kohno, Tokyo (JP); Akihiro Ishikawa, Kyoto (JP); Yoshinori Masuda, Kyoto (JP); Haruhide Udagawa, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 367 days.

(21) Appl. No.: 13/810,115

(22) PCT Filed: Jul. 16, 2010

(86) PCT No.: PCT/JP2010/062086
§ 371 (c)(1),
(2), (4) Date: Jan. 14, 2013

(87) PCT Pub. No.: WO2012/008047
PCT Pub. Date: Jan. 19, 2012

(65) Prior Publication Data
US 2013/0116521 A1   May 9, 2013

(51) Int. Cl.
| | |
|---|---|
| *A61B 5/1455* | (2006.01) |
| *G01N 21/359* | (2014.01) |
| *G01N 21/47* | (2006.01) |
| *A61B 5/145* | (2006.01) |
| *A61B 5/00* | (2006.01) |

(52) U.S. Cl.
CPC ......... *A61B 5/14553* (2013.01); *A61B 5/14546* (2013.01); *A61B 5/14552* (2013.01); *A61B 5/6814* (2013.01); *G01N 21/359* (2013.01); *G01N 21/474* (2013.01)

(58) Field of Classification Search
CPC ............. A61B 5/0059; A61B 5/14552; A61B 5/14553; A61B 5/6814; A61B 2562/0233; A61B 2562/046
See application file for complete search history.

(56) References Cited

U.S. PATENT DOCUMENTS

| | | | | |
|---|---|---|---|---|
| 4,998,186 | A  * | 3/1991 | Cocca ................ | A44C 15/0015 362/103 |
| 7,039,454 | B1 * | 5/2006 | Kaga .................... | A61B 5/1455 600/476 |
| 7,139,600 | B2 * | 11/2006 | Maki et al. .................... | 600/344 |
| 8,229,531 | B2 * | 7/2012 | Atsumori ............. | A61B 5/6814 600/344 |

* cited by examiner

*Primary Examiner* — Eric Winakur
(74) *Attorney, Agent, or Firm* — McDermott Will & Emery LLP (57) ABSTRACT

Provided is a holder which comprises at least two probe mount portions into which a light-transmitting probe for emitting light from the tip thereof or a light-receiving probe for receiving light through the tip thereof is inserted from above and is to be put on the head of a subject, the holder being characterized by further comprising: a linear backbone portion that extends in a first direction that is perpendicular to the above-described direction from above; and at least two linear branch portions that extend in a second direction that is perpendicular to the above-described direction from above and is different from the first direction, wherein the lower end portions of the probe mount portions protrude from the lower surface of the backbone portion or a branch portion and are tapered.

10 Claims, 10 Drawing Sheets

HOLDER AND LIGHT MEASUREMENT DEVICE EMPLOYING SAME

This application is a national stage of PCT/JP2010/062086 filed Jul. 16, 2010, the entire contents of which is hereby incorporated by reference.

TECHNICAL FIELD

The present invention relates to a holder and a light measuring device using the same, and in particular to a holder having a number of light transmitting points for illuminating a living body with light and a number of light receiving points for receiving light diffused from the living body, and for measuring information on the inside of a living body for a number of channels which are set for each pair of one light transmitting point and one light receiving point, and a light measuring device using the same.

BACKGROUND ART

In recent years, optical brain function imaging devices (light measuring devices) for a simple noninvasive measurement using light have been developed in order to observe brain activity. In such an optical brain function imaging device, the brain is irradiated with near infrared rays having three different wavelengths $\lambda_1$, $\lambda_2$ and $\lambda_3$ (780 nm, 805 nm and 830 nm, for example) from the light-transmitting probes placed on the surface of the head of the subject, and at the same time, the intensity $A(\lambda_1)$, $A(\lambda_2)$ and $A(\lambda_3)$ (information on the amount of received light) of the near infrared rays of each wavelength $\lambda_1$, $\lambda_2$ and $\lambda_3$ diffused from the brain is respectively detected by the light-receiving probes placed on the surface of the head.

In order to find the product [oxyHb] of the concentration of oxyhemoglobin in the cerebral blood vessels and the length of the light path and the product [deoxyHb] of the concentration of deoxyhemoglobin in the cerebral blood vessels and the length of the light path from the thus-gained information on the amount of received light $A(\lambda_1)$, $A(\lambda_2)$ and $A(\lambda_3)$, the Modified Beer-Lambert Law has been used to prepare simultaneous equations shown in the relational expressions (1), (2) and (3), for example, and these simultaneous equations have been solved (see Non-Patent Document 1). Furthermore, the product ([oxyHb]+[deoxyHb]) of the concentration of total hemoglobin and the length of the light path has been calculated from the product [oxyHb] of the concentration of oxyhemoglobin and the length of the light path and the product [deoxyHb] of the concentration of deoxyhemoglobin and the length of the light path.

$$A(\lambda_1)=E_O(\lambda_1)\times[\text{oxyHb}]+E_d(\lambda_1)\times[\text{deoxyHb}] \quad (1)$$

$$A(\lambda_2)=E_O(\lambda_2)\times[\text{oxyHb}]+E_d(\lambda_2)\times[\text{deoxyHb}] \quad (2)$$

$$A(\lambda_3)=E_O(\lambda_3)\times[\text{oxyHb}]+E_d(\lambda_3)\times[\text{deoxyHb}] \quad (3)$$

Here, $E_O(\lambda m)$ is the coefficient of absorbance of the oxyhemoglobin for the light of the wavelength $\lambda m$, and $E_d(\lambda m)$ is the coefficient of absorbance of the deoxyhemoglobin for the light of the wavelength $\lambda m$.

Figure 5:
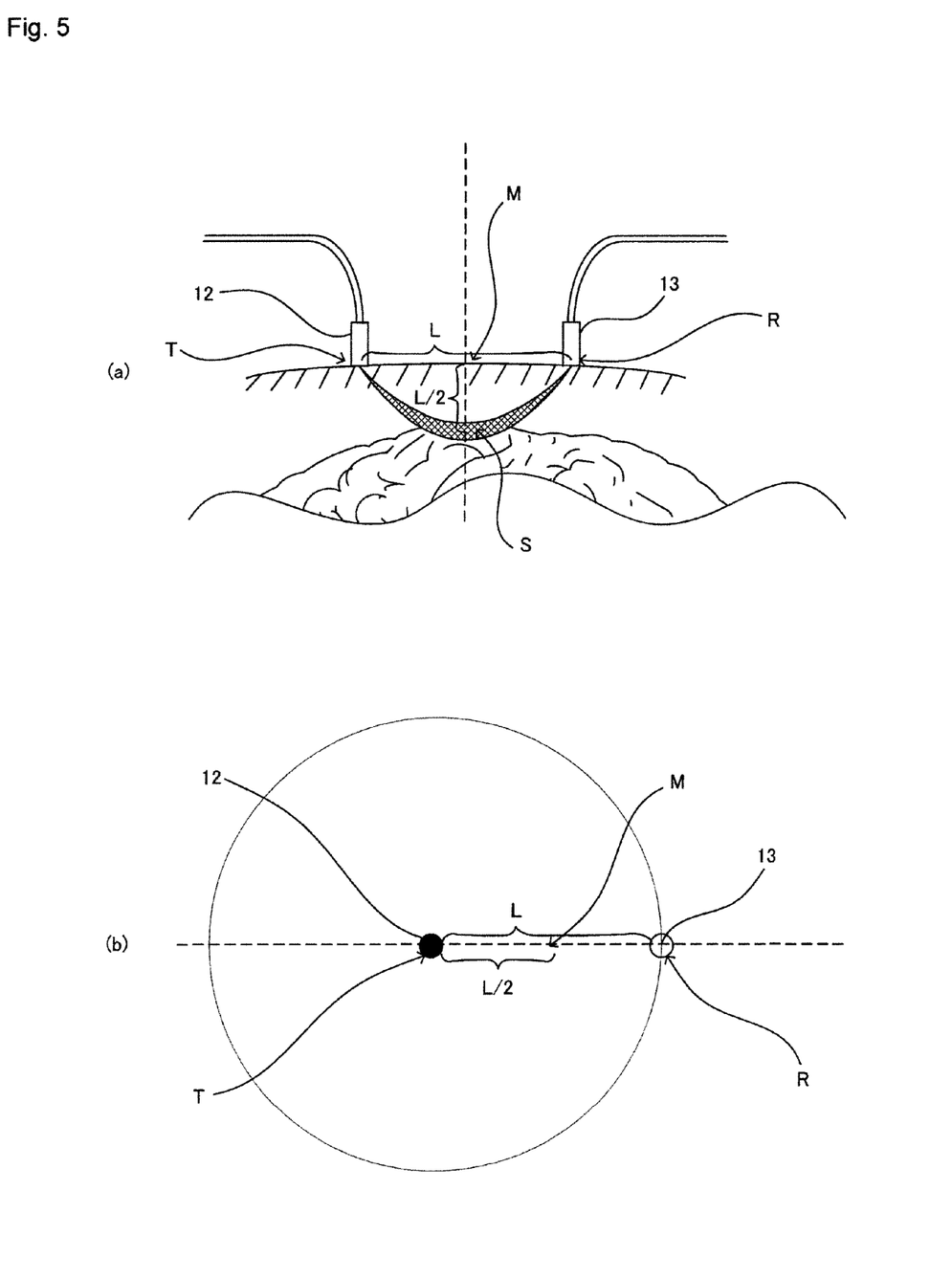
FIGS. 5(a) and 5(b) are diagrams showing the relationship between a pair of probes, a light-transmitting probe and a light-receiving probe, and the portion to be measured.

Here, the relationship between the distance between a light-transmitting probe and a light-receiving probe (channel) and the portion to be measured is described. FIG. 5(a) is a cross-sectional diagram showing the relationship between a pair of probes, a light-transmitting probe and a light-receiving probe, and the portion to be measured, and FIG. 5(b) is a plan diagram of FIG. 5(a).

A light-transmitting probe 12 is pressed against a light transmitting point T on the surface of the head of a subject, and at the same time, a light-receiving probe 13 is pressed against a light receiving point R on the surface of the head of the subject. Thus, light is emitted from the light-transmitting probe 12, and at the same time, the light diffused and absorbed from the surface of the head enters into the light-receiving probe 13. At this time, the light that has passed through the banana-shaped area (area to be measured) from among the light emitted from the light transmitting point T on the surface of the head reaches the light receiving point R on the surface of the head. As a result, information on the amount of received light $A(\lambda_1)$, $A(\lambda_2)$ and $A(\lambda_3)$ concerning the portion to be measured S of the subject at a depth of approximately L/2, which is half of the distance along the line connecting the light transmitting point T and the light receiving point R along the surface of the head of the subject from the mid-point M of the line L connecting the light transmitting point T and the light receiving point R along the surface of the head of the subject, is particularly gained from among the area to be measured.

In optical brain function imaging devices, a near infrared spectrometer, for example, is used in order to measure the change in the product [oxyHb] of the concentration of oxyhemoglobin and the length of the light path, the change in the product [deoxyHb] of the concentration of deoxyhemoglobin and the length of the light path, and the change in the product ([oxyHb]+[deoxyHb]) of the concentration of total hemoglobin and the length of the light path concerning a number of portions to be measured in the brain (see Patent Document 1).

Figure 6:
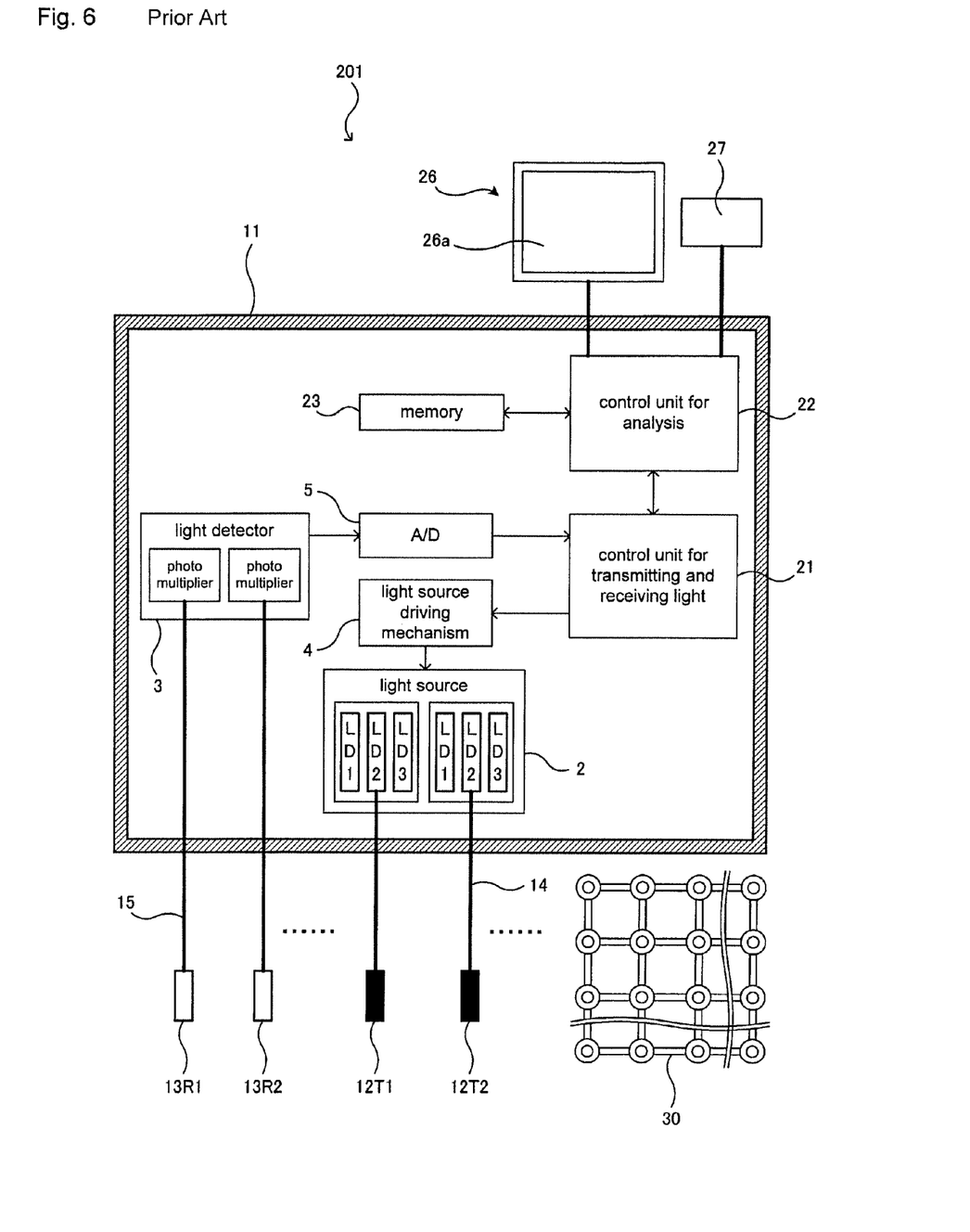
FIG. 6 is a block diagram schematically showing an example of the structure of a conventional near infrared spectrometer.

FIG. 6 is a block diagram schematically showing an example of the structure of a conventional near infrared spectrometer. Here, several optical fibers for transmitting light and several optical fibers for receiving light are omitted in order to simplify the drawing.

A near infrared spectrometer 201 has a housing 11 in a rectangular parallelepiped form.

A light source 2 for emitting light, a light source driving mechanism 4 for driving the light source 2, a light detector 3 for detecting light, an A/D converter 5, a control unit 21 for transmitting and receiving light, a control unit 22 for analysis and a memory 23 are provided inside the housing 11, and at the same time, 64 light-transmitting probes 12, 64 light-receiving probes 13, 64 optical fibers 14 for transmitting light, 64 optical fibers 15 for receiving light, a display 26 having a monitor screen 26a, and a keyboard (input device) 27 are provided outside the housing 11.

The light source driving mechanism 4 drives the light source 2 using a drive signal inputted from the control unit 21 for transmitting and receiving light. The light source 2 is made of semiconductor lasers LD1, LD2, LD3 and the like that can emit near infrared rays having three different wavelengths $\lambda_1$, $\lambda_2$ and $\lambda_3$, for example.

The light detector 3 is a detector for outputting a light reception signal (information on the amount of received light) $A(\lambda_1)$, $A(\lambda_2)$ or $A(\lambda_3)$ to the control unit 21 for transmitting and receiving light via the A/D converter 5 by detecting the respective near infrared rays and is a photomultiplier, for example.

The optical fibers 14 for transmitting light and the optical fibers 15 for receiving light are flexible lines with a diameter of 2 mm and a length of 2 meters to 10 meters and can convey near infrared rays in the direction of the axis so that the near infrared rays that have entered through one end pass through the inside so as to emit through the other end.

One optical fiber 14 for transmitting light is connected to one probe 12 for transmitting light and one semiconductor laser LD1, LD2 or LD3 in the light source 2 at the two ends so that the two are away from each other at a set length (2 meters to 10 meters).

One optical fiber 15 for receiving light is connected to one probe 13 for receiving light and one photomultiplier in the light detector 3 at the two ends so that the two are away from each other at a set length (2 meters to 10 meters).

Figure 7:
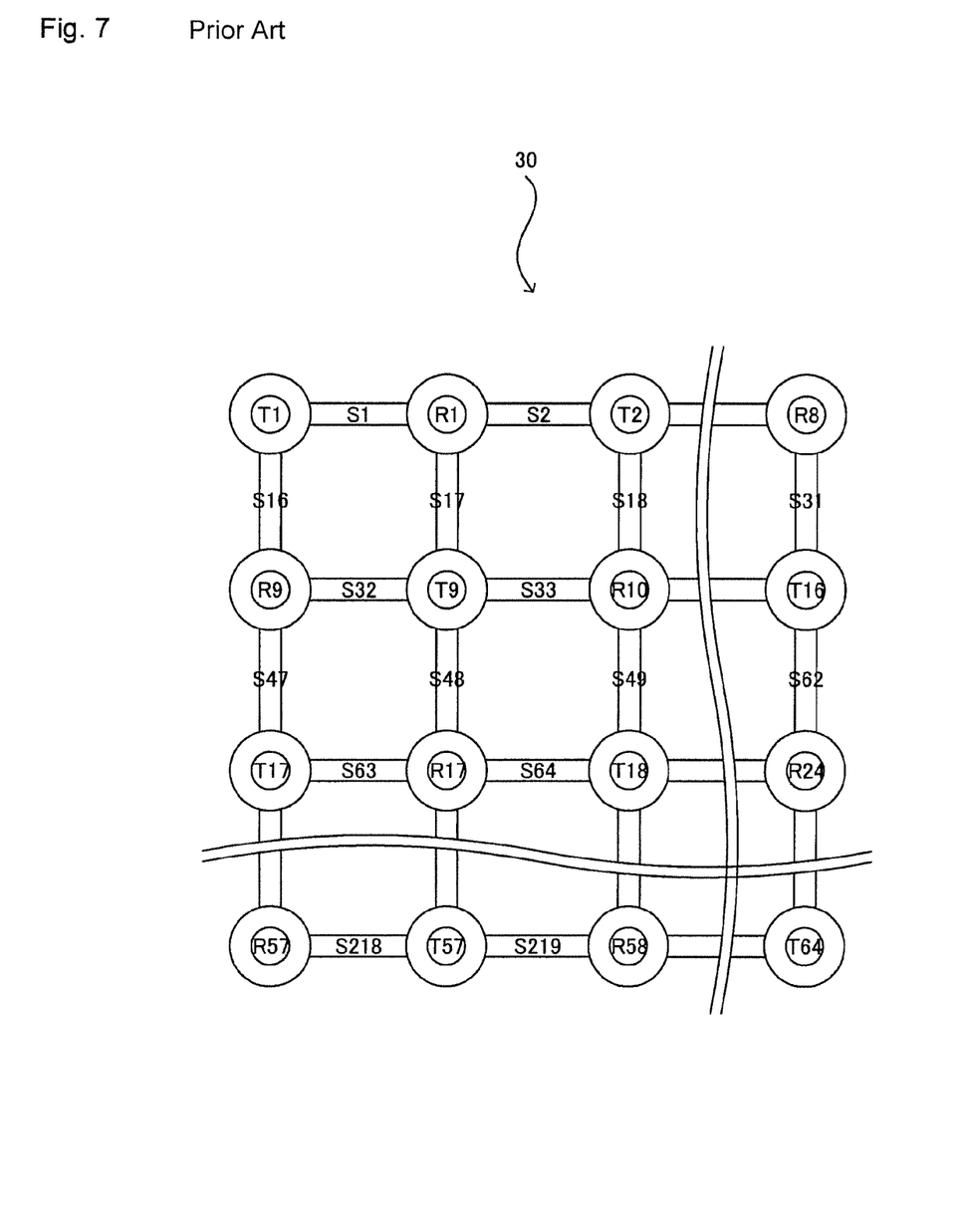
FIG. 7 is a plan diagram showing an example of the holder.

In this near infrared spectrometer 201, a holder 30 is used in order to make the 64 light-transmitting probes 12 and the 64 light-receiving probes 13 make contact with the surface of the head of a subject in a predetermined alignment. FIG. 7 is a plan diagram showing an example of the holder 30 into which 64 light-transmitting probes and 64 light-receiving probes are inserted.

The light-transmitting probes $12_{T1}$ to $12_{T64}$ and the light-receiving probes $13_{R1}$ to $13_{R64}$ are aligned alternately in a matrix of 16 in the longitudinal direction and 16 in the lateral direction. As a result, the distance between the light-transmitting probes 12 and the light-receiving probes 13 is constant so that the information on the amount of received light $A(\lambda_1)$, $A(\lambda_2)$ and $A(\lambda_3)$ is gained at a certain depth from the surface of the head. Here, a channel of 30 mm is generally used, and in the case where the channel is 30 mm, it is possible for the information on the amount of received light $A(\lambda_1)$, $A(\lambda_2)$ and $A(\lambda_3)$ to be gained at a depth of 15 mm to 20 mm from the mid-point of each channel. That is to say, the locations at a depth of 15 mm to 20 mm from the surface of the head approximately correspond to the portions on the surface of the brain, and thus, the amount of received light $A(\lambda_1)$, $A(\lambda_2)$ and $A(\lambda_3)$ concerning the brain activity is gained.

The curvature of the surface of the head differs depending on the sex, the age and the individual, and therefore, a holder that can be easily worn on the head with a different curvature of the surface has been proposed. In the holder, support portions for holding the light-transmitting probes 12 and the light-receiving probes 13 are aligned in a tetragonal lattice on the surface of the head, and the support portions are linked at a set distance (30 mm, for example) with connection portions that do not exhibit stretchability, and furthermore, the connection portions are rotatable by a predetermined angle or less with the support portions as a rotational axis in a plane through which the holder makes contact with the surface of the head (see Patent Document 2).

This holder 30 is provided with 128 socket parts 33 for fixing the light-transmitting probes 12 and the light-receiving probes 13, 232 connection parts 31 and 128 nut parts 32.

Figure 8:
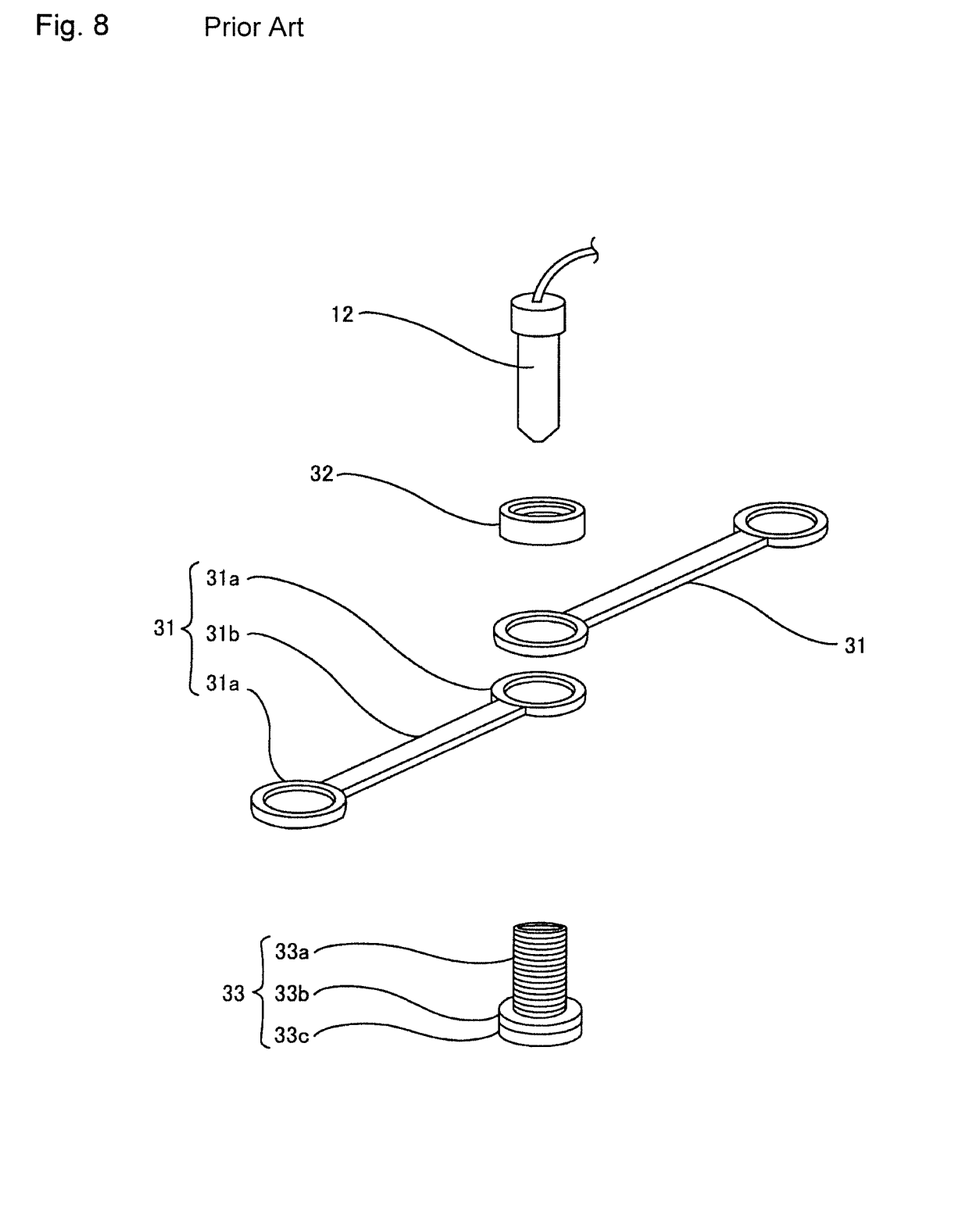
FIG. 8 is an exploded perspective diagram showing a light-transmitting probe, a nut part, two connection parts and a socket part.
Figure 9:
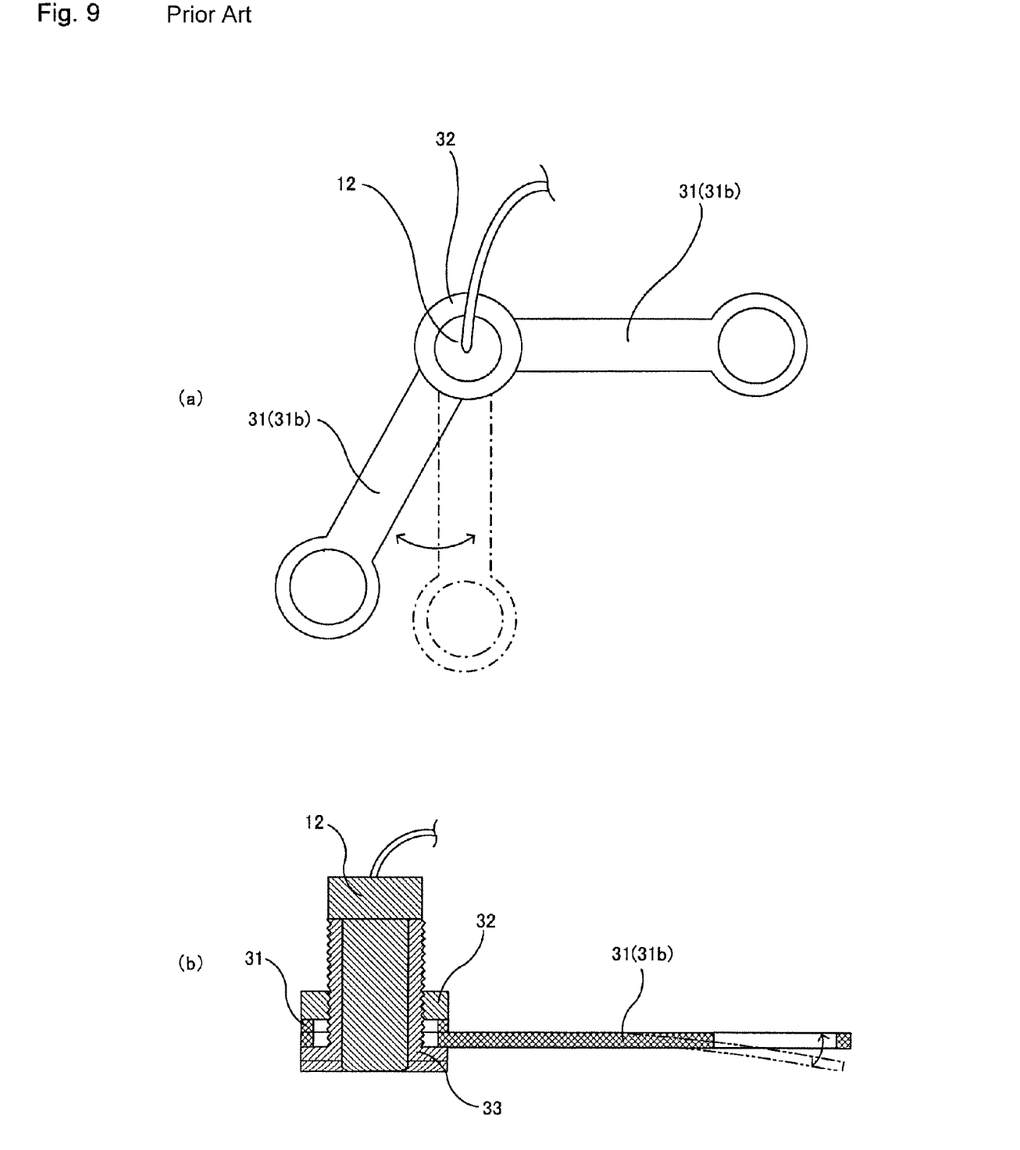
FIGS. 9(a) and 9(b) are diagrams showing the light-transmitting probe, the nut part, the two connection parts and the socket part after assembly.

Here, FIG. 8 is an exploded perspective diagram showing a light-transmitting probe 12, a nut part 32, two connection parts 31 and a socket part 33, and FIG. 9 is a diagram showing the light-transmitting probe 12, the nut part 32, the two connection parts 31 and the socket part 33 after assembly.

The connection parts 31 are plates in an I-shape. In addition, the connection parts 31 have insertion portions 31a in annular form at the two ends and a linking portion 31b for linking the insertion portions 31a at the two ends at a set distance. Circular through holes through which a socket part 33 is inserted are created at the center of the respective insertion portions 31a. In addition, the linking portion 31b has a width of 10 mm and a thickness of 0.1 mm with a set distance of 31.5 mm, which is the distance between the centers of the through holes at the two ends. The linking portion 31 is formed so as to have flexibility only in the direction of the thickness. That is to say, the insertion portions 31a at the two ends are always held at a channel length X.

The socket part 33 has a main body portion 33a in cylindrical form, a flange 33b in annular form and a bottom 33c in annular form so that a light-transmitting probe 12 or a light-receiving probe 13 can be inserted inside, and at the same time, the outside of the main body portion 33a is threaded so that the nut part 32 can be engaged.

The nut part 32 is in annular shape having a circular through hole, and the inside is threaded so that the main body portion 33a of the socket part 33 can be engaged. Here, the size of the through hole is greater than that of the main body portion 33a of the socket part 33 and is smaller than that of the flange 33b of the socket part 33 as viewed from the top.

As a result, the insertion portion 31a of a connection part 31 can be sandwiched between the flange 33b of the socket part 33 and the nut part 32 so as to be fixed when the main body portion 33a of the socket part 33 is screwed into the nut part 32.

The light-transmitting probes 12 are in cylindrical form (diameter: 5 mm, for example), which can fix a socket part 33. An optical fiber 14 for transmitting light (diameter: 2 mm, for example) that is connected to the light source 2 is fixed to the inside of a light-transmitting probe 12 with a spring in between so that light can be emitted from the end of the optical fiber 14 for transmitting light.

In addition, the light-receiving probes 13 have the same structure as the light-transmitting probes 12 and are in cylindrical form (diameter: 5 mm, for example), which can fix a socket part 33. Thus, an optical fiber 15 for receiving light (diameter: 2 mm, for example) that is connected to the light detector 3 is fixed to the inside of a light-receiving probe 13 with a spring in between so that light can be received by the end of the optical fiber 15 for receiving light.

A holder 30, as in FIG. 7, is made of 128 socket parts 33, 232 connection parts 31 and 128 nut parts 32, for example. A doctor or another person who carries out the measurement slightly loosens the screw mechanism between the flange 33b of a socket part 33 and a nut part 32 so that one connection part 31 and another connection part 31 are fixed to each other by forming a desired angle around the socket part 33 as viewed from above, as shown in FIG. 9(a), and at the same time, the linking portion 31b of the connection part 31 can deform due to its flexibility, as shown in FIG. 9(b), so as to have a curvature that matches the surface of the head, and thus, this holder 30 can make close contact with the surface of the head when being worn. The doctor or the other person firmly fixes the screw mechanism between the flange 33b of the socket part 33 and the nut part 32 in the thus-deformed state. Then, the holder 30 does not return to a flat state, and as a result, the curvature is maintained. Finally, the doctor or the other person inserts the light-transmitting probes 12 and the light-receiving probes 13 into the socket parts 33 in a predetermined alignment.

In the positional relationship between these 64 light-transmitting probes $12_{T1}$ to $12_{T64}$ and 64 light-receiving probes $13_{R1}$ to $13_{R64}$, it is necessary to adjust the timing in the emissions of light from the light-transmitting probes 12 and the receptions of light by the light-receiving probes 13 so that one light-receiving probe 13 receives light emitted from only one light-transmitting probe 12 instead of receiving light emitted from a number of light-transmitting probes 12 simultaneously. Therefore, the memory 23 stores a control table showing the timing according to which the light source 2 emits light and the light detector 3 detects the light.

The control unit 21 for transmitting and receiving light where this control table is stored in the memory 23 outputs a drive signal for allowing one light-transmitting probe 12 to transmit light to the light source driving mechanism 4, and at the same time allows the light detector 3 to detect the light reception signal (information on the amount of received light) received by the light-receiving probe 13.

As a result, as shown in FIG. 7 as a plan view, a total of 232 pieces (S1 to S232) of information on the amount of received light A ($\lambda_1$), A ($\lambda_2$) and A ($\lambda_3$) is collected.

Thus, the control unit 22 for analysis finds the change in the product [oxyHb] of the concentration of oxyhemoglobin and the length of the light path, the change in the product [deoxyHb] of the concentration of deoxyhemoglobin and the length of the light path, and the change in the product ([oxyHb]+[deoxyHb]) of the concentration of total hemoglobin and the length of the light path from the intensity of the light that has passed of each wavelength (wavelength of light absorbed by oxyhemoglobin and the wavelength of light absorbed by deoxyhemoglobin) by using the relational expressions (1), (2) and (3) on the basis of the total of the 232 pieces of information on the amount of received light A ($\lambda_1$), A ($\lambda_2$) and A ($\lambda_3$).

PRIOR ART DOCUMENTS

Patent Documents

Patent Document 1: Japanese Unexamined Patent Publication 2001-337033
Patent Document 2: Japanese Unexamined Patent Publication 2009-077841

Non-Patent Document

Non-Patent Document 1: Factors affecting the accuracy of near-infrared spectroscopy concentration calculations for focal changes in oxygenation parameters, Neuro Image 18, 865-879, 2003

SUMMARY OF THE INVENTION

Problem to be Solved by the Invention

In order for the above-described holder 30 to be made to make close contact with the surface of the head of a subject, a doctor or another person needs to change the form of the holder 30 so that the surface thereof has such a curvature as to match the surface of the head by adjusting the angle to a desired angle between one connection part 31 and another connection part 31 around a socket part 33 as the rotational axis, and then firmly secure the screw mechanism between the flange 33b and the nut part 32 of the socket part 33.

Accordingly, in the case where the above-described holder 30 is made to make close contact with the surface of the head of a subject, the screw mechanisms between the flanges 33b and the nut parts 32 of a great number (128) of socket parts 33 must be firmly fixed, which is very troublesome for the doctor or the other person and is very stressful for the subject because he or she needs to keep still for a long period of time.

Furthermore, light-transmitting probes $12_{T1}$ to $12_{T64}$ and light-receiving probes $13_{R1}$ to $13_{R64}$ are attached to the holder 30 after the holder 30 is made to make close contact with the surface of the head of a subject. There is hair on the surface of the head of a human body, and therefore, the ends of the light-transmitting probes $12_{T1}$ to $12_{T64}$ and the light-receiving probes $13_{R1}$ to $13_{R64}$ must be made to make contact with the surface of the head while avoiding the hair, which makes it necessary to push the hair aside when attaching the light-transmitting probes $12_{T1}$ to $12_{T64}$ and the light-receiving probes $13_{R1}$ to $13_{R64}$.

Therefore, when the light-transmitting probes $12_{T1}$ to $12_{T64}$ and the light-receiving probes $13_{R1}$ to $13_{R64}$ are attached to the holder 30, the hair must be pushed aside, which is very troublesome for the doctor or the other person and is very stressful for the subject because he or she needs to keep still for a long period of time.

In the case where a change in the blood flow through the portions within the brain of a subject as time elapses is measured when the subject is exercising, such as for rehabilitation, it is not necessary to collect information on the amount of received light A ($\lambda_1$), A ($\lambda_2$) and A ($\lambda_3$) in the 232 portions to be measured (S1 to S232), and instead, information on the amount of received light A ($\lambda_1$), A ($\lambda_2$) and A ($\lambda_3$) only in portions desired to be measured, for example, eight portions, needs to be collected. Therefore, only four light-transmitting probes $12_{T1}$ to $12_{T4}$ from among the 64 light-transmitting probes $12_{T1}$ to $12_{T64}$ and only four light-receiving probes $13_{R1}$ to $13_{R4}$ from among the 64 light-receiving probes $13_{R1}$ to $13_{R64}$ need to be attached. However, it still takes approximately one hour for the doctor or the other person to attach the holder 30 to the head of a subject, and then attach the light-transmitting probes $12_{T1}$ to $12_{T4}$ and the light-receiving probes $13_{R1}$ to $13_{R4}$ to the holder 30, though the subject only exercises for approximately one hour, such as for rehabilitation. That is to say, the time for preparation during which the subject puts the holder 30 and the light-transmitting probes $12_{T1}$ to $12_{T4}$ and the light-receiving probes $13_{R1}$ to $13_{R4}$ on the head is very long in comparison with the time during which the subject exercises, such as for rehabilitation.

Furthermore, some subjects exercise everyday, such as for rehabilitation, and in the case where the subject exercises at home, his or her family attaches the holder 30 and the light-transmitting probes $12_{T1}$ to $12_{T4}$ and the light-receiving probes $13_{R1}$ to $13_{R4}$ to the head of the subject, which is very troublesome.

Means for Solving Problem

In order to solve these problems, the present applicant previously came up with an idea that a holder in comb shape can push hair aside when being put on the head by a subject so that the subject can precisely put it on in a short period of time, even when the subject is alone, and applied this holder for a patent.

However, annular protrusions are formed on the lower surface of the holder in comb shape when light-transmitting probes in columnar form (diameter: 5 mm, for example) and light-receiving probes in columnar form (diameter: 5 mm, for example) are inserted into circular through holes, and these protrusions resulting from the insertion of the light-transmitting probes and the light-receiving probes may be an obstacle when the holder in comb shape is put on by pushing the hair aside.

Therefore, the present applicant has found protrusions that are tapered in a certain direction on the lower surface of the holder in comb shape having branch portions.

That is to say, the holder according to the present invention is provided with at least two probe mount portions, into which a light-transmitting probe for emitting light from the tip thereof or a light-receiving probe for receiving light through the tip thereof is inserted from above, and is to be put on the head of a subject, and the holder is further provided with: a linear backbone portion extending in a first direction that is perpendicular to the above-described direction from above; and at least two linear branch portions extending in a second direction that is perpendicular to the above-described direction from above and is different from said first direction, wherein the above-described light-transmitting probe or the above-described light-receiving probe is attached so that a lower end portion thereof protrudes from a lower surface of the above-described backbone portion or a branch portion and is tapered in the above-described second direction.

Here, the "first direction" and the "second direction" are any directions predetermined by the designer of the holder or the like, and for example, the second direction is the direction from the front to the rear in which the holder can be easily moved while pushing the hair aside.

In addition, "tapered in the second direction" refers to the structure that functions to push the hair aside, and a triangle having an apex in the second direction, an ellipse of which the longer diameter runs in the second direction, and a diamond or a quadrilateral of which a diagonal line runs in the second direction can be cited as examples. Here, circles do not function to push the hair aside because the force functions equally in every direction, and therefore are not referred to as being "tapered in the second direction."

The holder according to the present invention is provided with a linear backbone portion extending in the first direction and at least two linear branch portions extending in the second direction. That is to say, the holder is in comb shape. In addition, lower portions of the light-transmitting probes and the light-receiving probes that are tapered in the second direction are attached to the branch portions of the holder according to the present invention. Therefore, a subject moves the holder in the second direction while pushing the hair aside when the holder is put on the head.

Effects of the Invention

As described above, the holder according to the present invention can be precisely put on the head of a subject in a short period of time, even when the subject is alone.

Other Means for Solving the Problem and Other Effects of the Invention

In the holder according to the present invention, the above-described probe mount portions have a through hole into which the above-described light-transmitting probe or the above-described light-receiving probe is inserted; and a lower end portion of the above-described probe mount portions protrudes from a lower surface of the above-described backbone portion or a branch portion and is tapered in the above-described second direction.

In addition, in the holder according to the present invention, a lower end portion of the above-described probe mount portions is in elliptical form having the longer diameter in the above-described second direction as viewed from below.

Furthermore, in the holder according to the present invention, the above-described branch portions are tapered in the above-described second direction.

Branch portions that are tapered in the second direction and lower end portions of the light-transmitting probes and the light-receiving probes that are tapered in the second direction are attached to the holder according to the present invention. Therefore, a subject can very easily move the holder in the second direction while pushing hair aside when the holder is put on the head.

Moreover, the light measurement device according to the present invention is provided with: the holder as described above; a light-transmitting probe for emitting light towards the above-described subject; a light-receiving probe for receiving light emitted from the above-described subject; and a control unit for acquiring measurement data on the brain activity of the above-described subject by controlling the above-described light-transmitting probe and the above-described light-receiving probe.

BEST MODE FOR CARRYING OUT THE INVENTION

In the following, the preferred embodiments of the present invention are described in reference to the drawings. Here, the present invention is not limited to the below-described embodiments, but various modifications are naturally included as long as the gist of the present invention is not deviated from.

Figure 1:
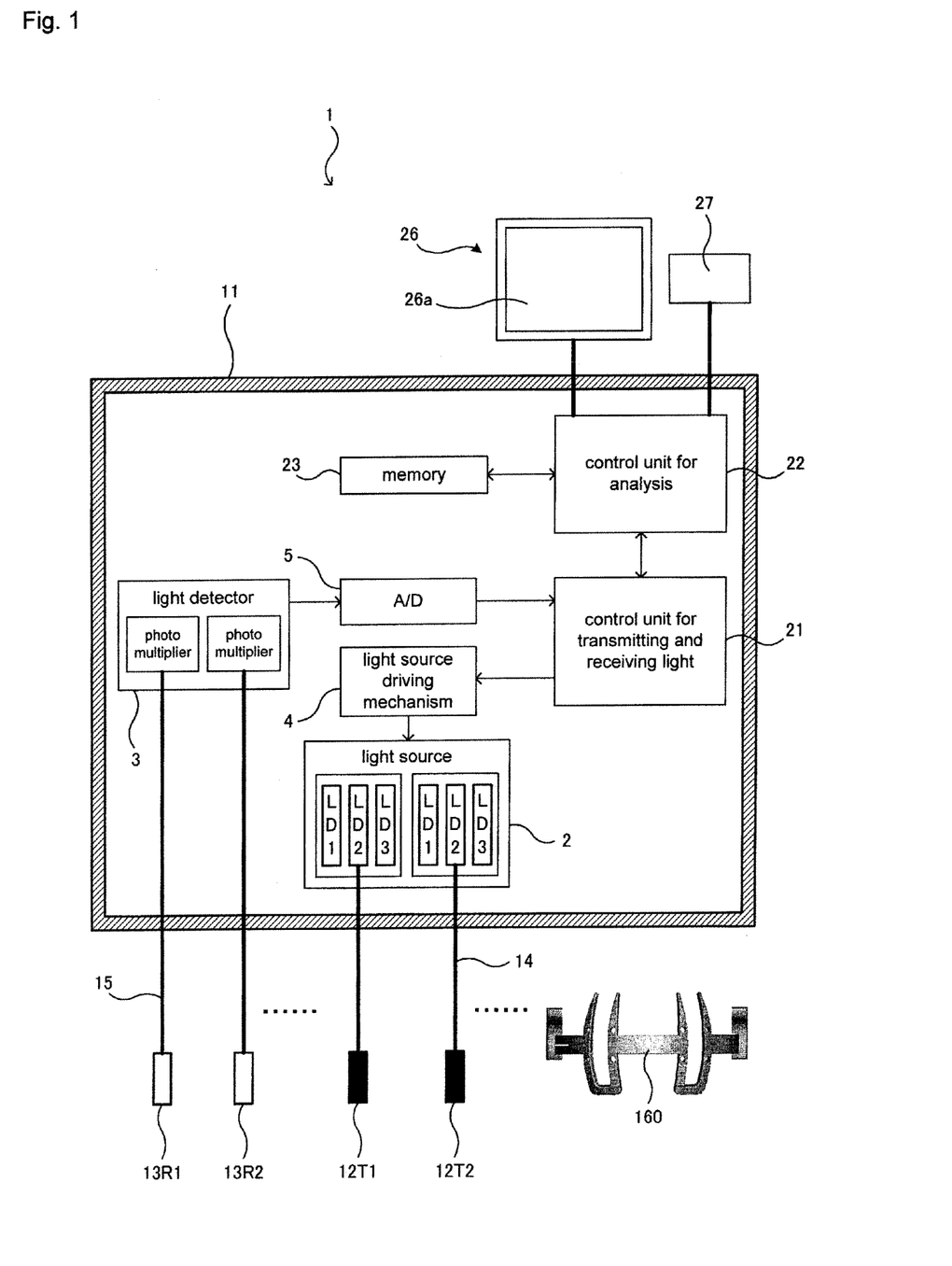
FIG. 1 is a block diagram schematically showing the structure of the light measurement device according to one embodiment of the present invention.
Figure 2:
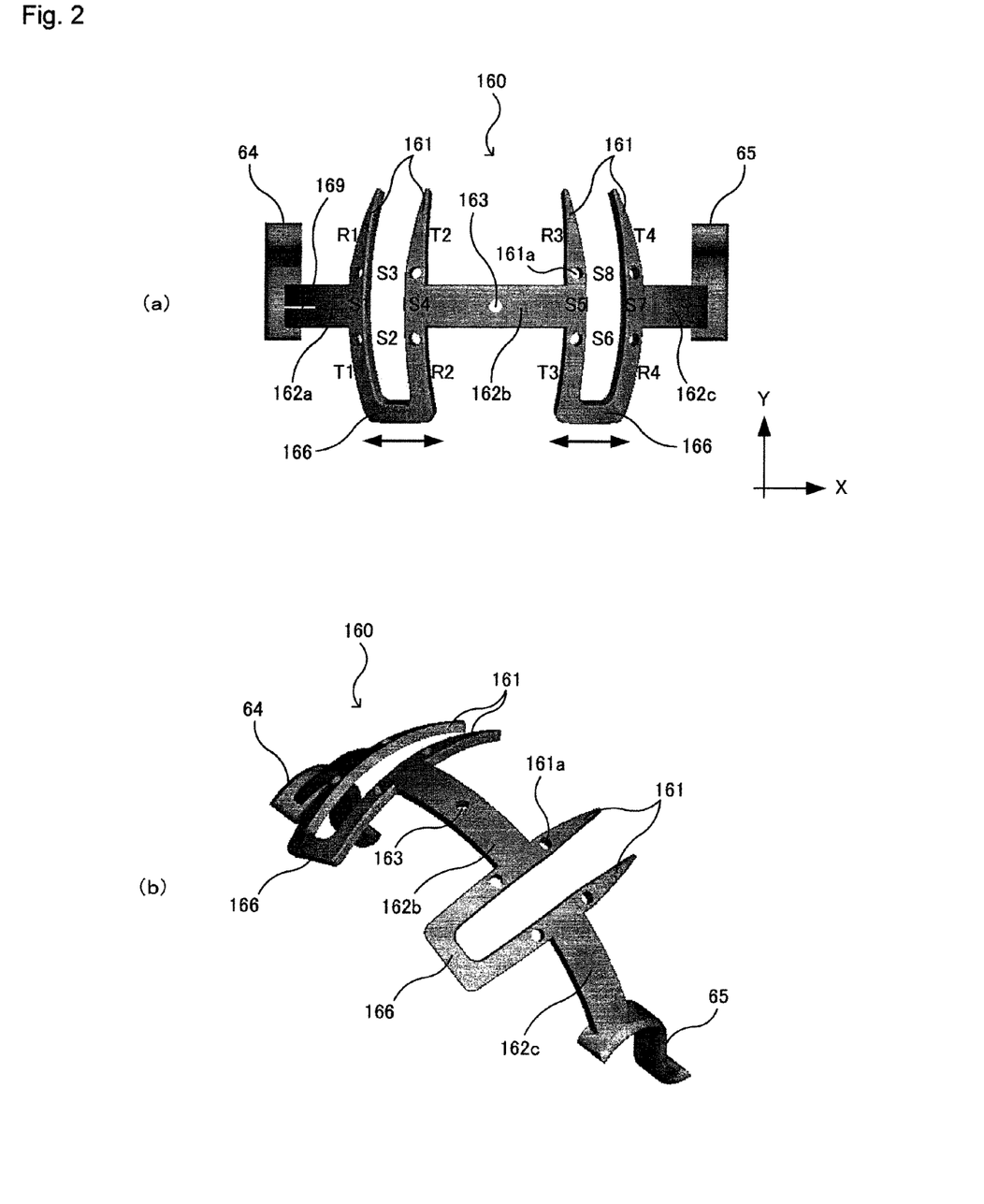
FIGS. 2(a) and 2(b) are diagrams showing an example of the holder.

FIG. 1 is a block diagram schematically showing the structure of the light measurement device according to one embodiment of the present invention. In addition, FIGS. 2(a) and 2(b) are diagrams showing an example of the holder. The same symbols are attached to the same components as in the near infrared spectrometer 201. In addition, the light measurement device 1 is to be used in a hospital.

The light measurement device 1 has a housing 11 in rectangular parallelepiped form.

A light source 2 for emitting light, a light source driving mechanism 4 for driving the light source 2, a light detector 3 for detecting light, an A/D converter 5, a control unit for transmitting and receiving light 21, a control unit for analysis 22 and a memory 23 are provided inside the housing 11, and at the same time, 64 light-transmitting probes 12, 64 light-receiving probes 13, 64 optical fibers 14 for transmitting light, 64 optical fibers 15 for receiving light, a display 26 having a monitor screen 26a, and a keyboard (input device) 27 are provided with the outside of the housing 11.

Here, a holder 160 is described below. FIG. 2(a) is a plan diagram showing a holder, and FIG. 2(b) is a perspective diagram showing the holder in FIG. 2(a).

The holder 160 is provided with a linear backbone portion 162, four linear branch portions 161, two linking portions 166, a right end portion 64 that hooks onto the right ear and a left end portion 65 that hooks onto the left ear.

The backbone portion 162 is divided into three pieces: a right side portion 162a, a center portion 162b and a left side portion 162c, and extends in the direction X (first direction) so as to be in an arc form as viewed from the front with spaces between the right side portion 162a and the center portion 162b as well as between the center portion 162b and the left side portion 162c. In addition, the right side portion 162a, the center portion 162b and the left side portion 162c have a width of 15 mm and a thickness of 0.1 mm, for example.

A disposition reference point 163 is defined as a circular through hole (diameter: 7 mm, for example) at the center of the center portion 162b. In addition, a disposition reference line 169 is defined as a linear mark extending in the direction X in the right side portion 162a.

Here, it has been preset for the holder 160 that a first specific point is the vertex, and thus, the disposition reference point 163 matches the vertex when the holder 160 is put on the head. In addition, the disposition reference line 169 matches the line for connecting the vertex and the right ear when the holder 160 is put on the head.

The branch portions 161 extend in the direction Y (second direction) that is perpendicular to the direction X and have a width of 15 mm, a thickness of 0.1 mm and a length of 90 mm, for example. Furthermore, probe mount portions 161a having a through hole in circular form as viewed from above (diameter: 5 mm, for example) are formed in the locations 30 mm and 61.5 mm away from first ends of the branch portions 161 towards second ends.

In addition, a linking portion 166 is formed so as to link one end of the first branch portion 161 to one end of the second branch portion 161 with a distance of 31.5 mm in the direction X between them. That is to say, a first U-shaped body is formed. As a result, the probe mount portions 161a form a first square with sides of 31.5 mm.

Furthermore, a linking portion 166 is formed so as to link one end of the third branch portion 161 to one end of the fourth branch portion 161 with a distance of 31.5 mm in the direction X between them. That is to say, a second U-shaped body is formed. As a result, the probe mount portions 161a form a second square with sides of 31.5 mm.

In addition, the other ends of the branch portions 161 are tapered in the second direction in order to push the hair aside.

Figure 4:
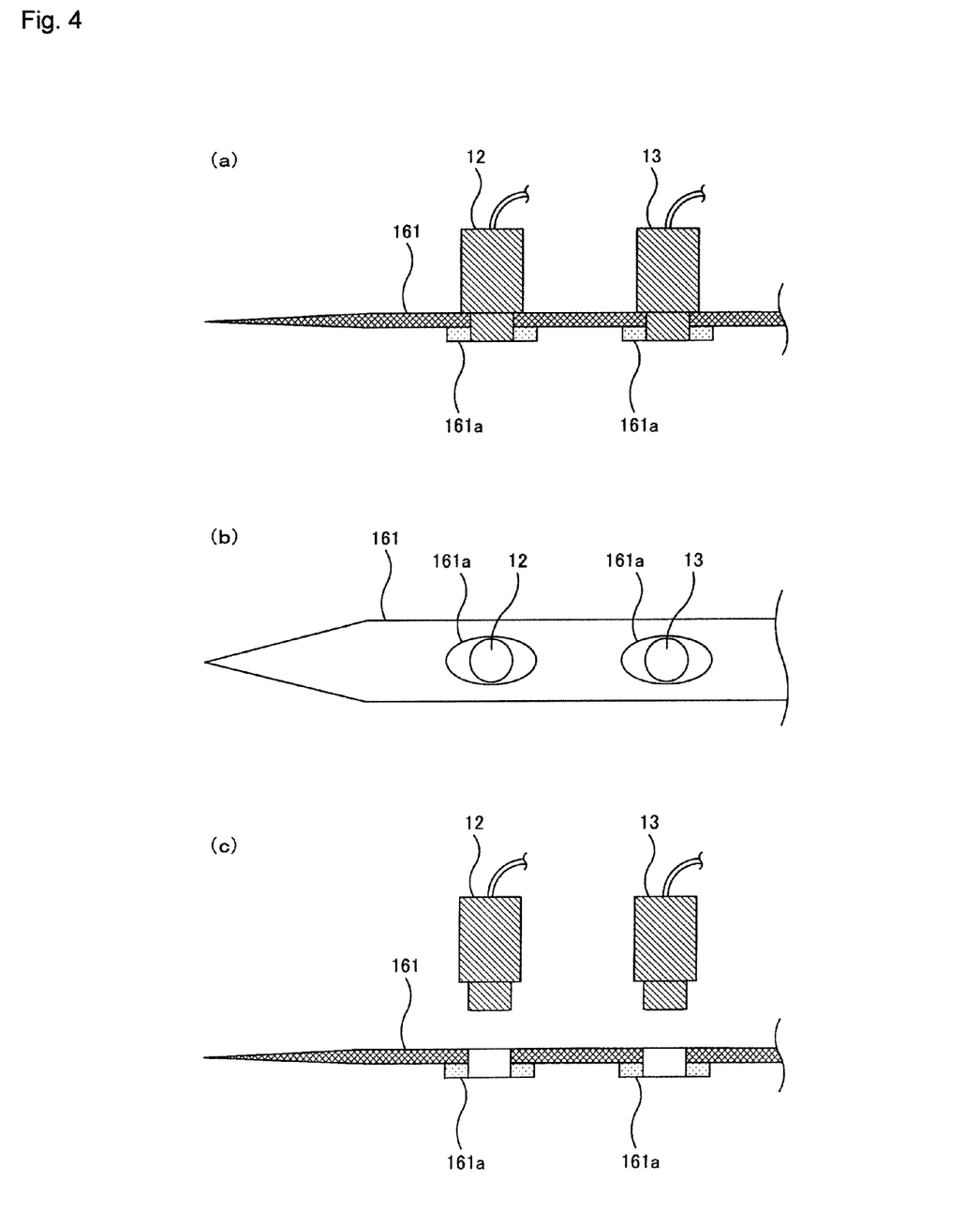
FIGS. 4(a) to 4(c) are diagrams showing the example of the holder.

FIG. 4(a) is a cross-sectional diagram showing part of a branch portion 161 of the holder 160 to which a light-transmitting probe 12 and a light-receiving probe 13 are attached, FIG. 4(b) is a plan diagram showing the branch portion 161 of the holder 160 in FIG. 4(a) as viewed from the rear, and FIG. 4(c) is a cross-sectional diagram showing part of the branch portion 161 of the holder 160 from which the light-transmitting probe 12 and the light-receiving probe 13 are disengaged.

The lower end portions of the probe mount portions 161a protrude from the lower surface of the branch portion 161. Furthermore, the lower end portions of the probe mount portions 161a are in elliptical form that is long in the direction Y (second direction) in order to push the hair aside. That is to say, the lower end portions of the probe mount portions 161a are tapered in the direction Y (second direction).

In addition, it is possible to insert a light-transmitting probe 12 or a light-receiving probe 13 into the circular through holes created in the probe mount portions 161a so as to be fixed. As a result, as shown in FIG. 2(a) as a plan view, a total of eight pieces (S1 to S8) of information on the amount of received light A ($\lambda_1$), A ($\lambda_2$) and A ($\lambda_3$) can be collected when the light-transmitting probes $12_{T1}$ to $12_{T4}$ and the light-receiving probes $13_{R1}$ to $13_{R4}$ are inserted into the probe mount portions 161a with the corresponding numbers.

Figure 3:
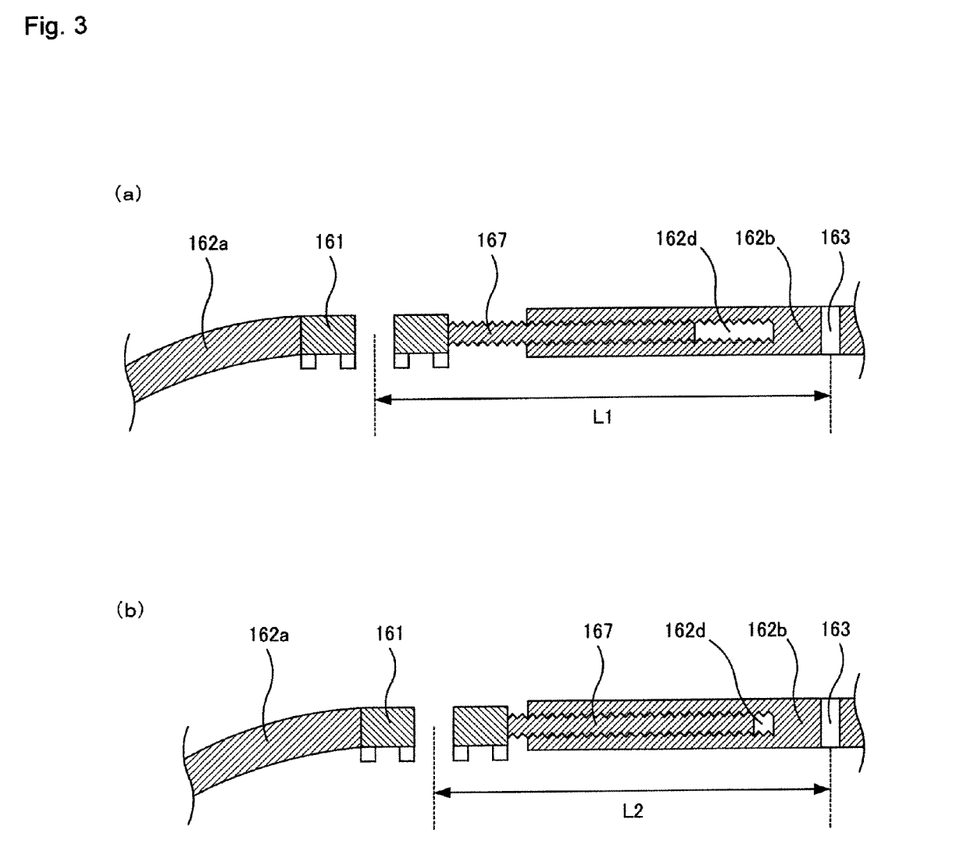
FIGS. 3(a) and 3(b) are diagrams showing the example of the holder.

In addition, FIG. 3(a) is a cross-sectional diagram showing part of the holder 160, and FIG. 3(b) is a cross-sectional diagram showing part of the holder 160 in a different state from that in FIG. 3(a).

The right side portion 162a is connected to the left side of the first branch portion 161 at the center, and at the same time, an insertion plate 167 that extends by a predetermined distance to the right is formed on the right side of the second branch portion 161 at the center. Meanwhile, an insertion hole 162d that extends by a predetermined distance to the right is created on the left side of the center portion 162b (see FIGS. 3(a) and 3(b)). Here, the surfaces of the insertion plate 167 and the insertion hole 162d have been processed so as to be rugged.

As a result, as shown in FIGS. 3(a) and 3(b), the insertion plate 167 can be inserted into the insertion hole 162d so that the insertion hole 162d and the insertion plate 167 can be engaged over a distance L1 or L2. That is to say, the first U-shaped body is movable in the direction X relative to the center portion 162b.

In addition, the left side portion 162c is connected to the right side of the fourth branch portion 161 at the center, and at the same time, an insertion plate (not shown) that extends by a predetermined distance to the left is formed on the left side of the third branch portion 161 at the center. Meanwhile, an insertion hole (not shown) that extends by a predetermined distance to the left is created on the right side of the center portion 162b. Here, the surfaces of the insertion plate and the insertion hole have been processed so as to be rugged.

As a result, the insertion plate can be inserted into the insertion hole so that the insertion hole and the insertion plate can be engaged over a desired distance. That is to say, the second U-shaped body is movable in the direction X relative to the center portion 162b.

The right end portion 64 is connected to the left end of the right side portion 162a and can hook onto the right ear. In addition, the left end portion 65 is connected to the right end of the left side portion 162c and can hook onto the left ear.

The material for forming the backbone portion 162, the branch portions 161, the linking portions 166, the right end portion 64 and the left end portion 65 is not particularly limited, but polypropylene, polyvinyl chloride, polyacetal and metals can be cited as examples.

In addition, the material for forming the probe mount portions 161a is not particularly limited, but polypropylene, polyvinyl chloride, polyacetal and metals can be cited as examples.

In the thus-formed light measuring device 1, first, a subject inserts the light-transmitting probes $12_{T1}$ to $12_{T4}$ and the light-receiving probes $13_{R1}$ to $13_{R4}$ into the probe mount portions 161a of the holder 160 in a predetermined alignment.

Next, the subject puts the holder 160 on the head in such a manner that the holder 160 pushes the hair aside with the branch portions 161 and the probe mount portions 161a when moved from the front towards the rear of the head.

Thus, the subject, while checking the disposition reference point 163 and the disposition reference line 169 with his or her fingers, adjusts the position of the holder so that the disposition reference point 163 matches the vertex, and at the same time, the disposition reference line 169 matches the line for connecting the vertex and the nasion.

Furthermore, the holder 160 is fixed onto the head with the right end portion 64 and the left end portion 65.

As described above, in the light measuring system 1 according to the present invention, a subject by himself or herself can precisely put the holder 160 on his or her own head in a short period of time.

Other Embodiments (1) Though in the above-described light measuring device 1 the structure allows the holder 160 to be put on the head when being moved from the front towards the rear of the head, the structure may allow the holder to be put on the head when being moved from the right side towards the left side of the head.

(2) Though in the above-described light measuring device 1 the structure allows four light-transmitting probes $12_{T1}$ to $12_{T4}$ and four light-receiving probes $13_{R1}$ to $13_{R4}$ to be attached to the holder 160, the structure may allow eight light-transmitting probes and eight light-receiving probes to be attached to the holder or may allow two light-transmitting probes and two light-receiving probes to be attached to the holder.

Figure 10:
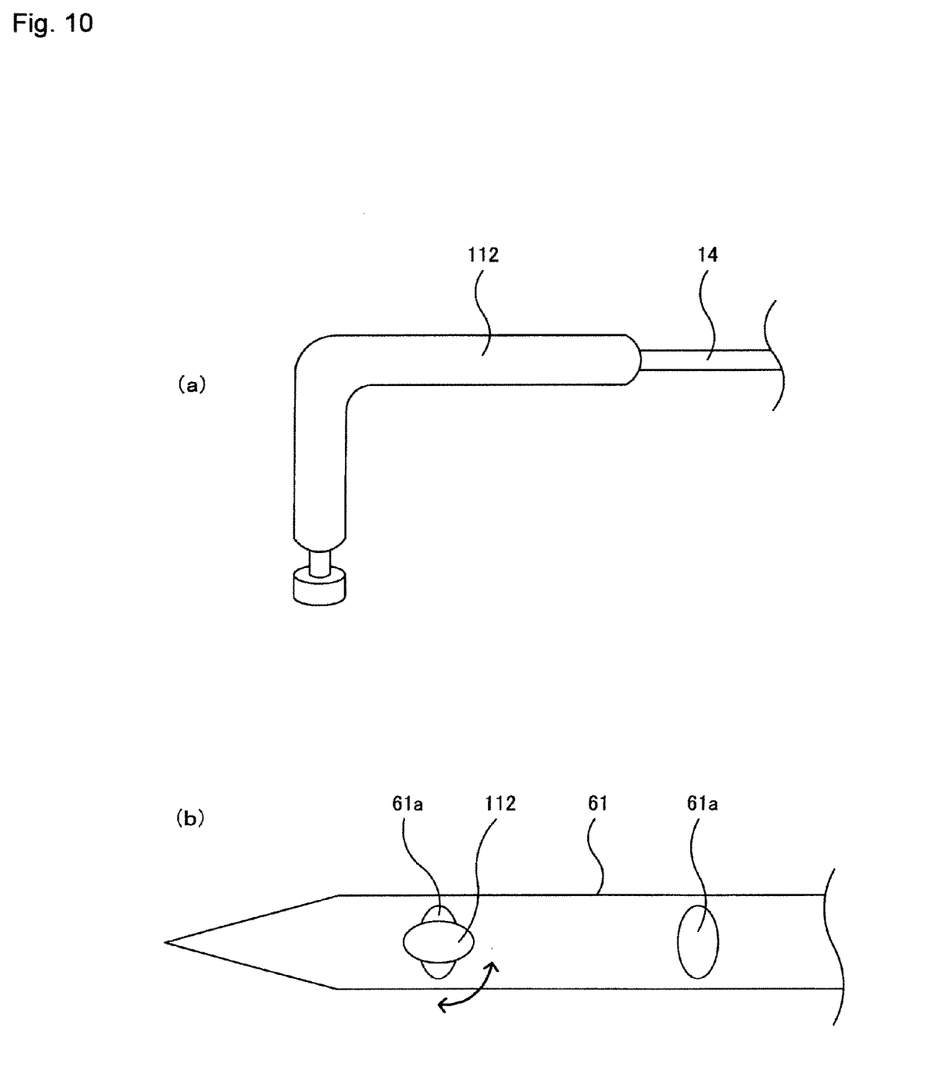
FIGS. 10(a) and 10(b) are diagrams showing another example of a light-transmitting probe and part of the holder.

(3) Though in the above-described light measuring device 1 the structure has the probe mount portions 161a having a through hole in circular form as viewed from above, the structure may have probe mount portions 61a having a through hole in elliptical form as viewed from above to which an elliptical light-transmitting probe 112 can be attached (see FIGS. 10(a) and 10(b)).

INDUSTRIAL APPLICABILITY

The present invention can be applied to alight measuring device for acquiring information on the inside of a living body by irradiating the inside of the living body with light.

EXPLANATION OF SYMBOLS

1: light measuring device
11: housing
12: light-transmitting probe
13: light-receiving probe
14: optical fiber for transmitting light
15: optical fiber for receiving light
22: control unit for analysis
26: display
27: keyboard (input device)
160: holder
161: branch portion
161a: probe mount portion
162: backbone portion
163: disposition reference point

The invention claimed is:

1. A holder configured to be place on a head of a subject and to hold a light-transmitting probe for emitting light to the head and a light-receiving probe for receiving light from the head, the holder comprising:
   a linear backbone portion extending in a first direction; and
   at least two linear branch portions extending in a second direction different from said first direction, wherein
   one of the at least two linear branch portions has at least one of probe mount portions for receiving the light-transmitting probe and the light-receiving probe, respectively, the probe mount portions being configured to allow tips of the light-transmitting probe and the light-receiving probe to project from the at least one of the two linear branch portions toward the side of the head,
   the probe mount portions have supports for supporting the tips, respectively, and
   each support tapers off in the second direction in a plan view.

2. The holder according to claim 1, wherein said probe mount portions have a through hole into which said light-transmitting probe or said light-receiving probe is inserted.

3. The holder according to claim 2, wherein each support has an elliptical form, in plan view, having the longer diameter in said second direction.

4. The holder according to claim 2, wherein said branch portions are tapered in said second direction.

5. A light measurement device comprising:
   the holder according to claim 2,
   one or a plurality of light-transmitting probes for emitting light towards said subject;
   one or a plurality of light-receiving probes for receiving light diffused and absorbed from said subject; and
   a control unit for acquiring measurement data on the brain activity of said subject by controlling said light-transmitting probes and said light-receiving probes.

6. The holder according to claim 3, wherein said branch portions are tapered in said second direction.

7. A light measurement device comprising:
   the holder according to claim 3,
   one or a plurality of light-transmitting probes for emitting light towards said subject;
   one or a plurality of light-receiving probes for receiving light diffused and absorbed from said subject; and
   a control unit for acquiring measurement data on the brain activity of said subject by controlling said light-transmitting probes and said light-receiving probes.

8. A light measurement device comprising:
   the holder according to claim 1,
   one or a plurality of light-transmitting probes for emitting light towards said subject;
   one or a plurality of light-receiving probes for receiving light diffused and absorbed from said subject; and
   a control unit for acquiring measurement data on the brain activity of said subject by controlling said light-transmitting probes and said light-receiving probes.

9. The holder according to claim 1, wherein said branch portions are tapered in said second direction.

10. A light measurement device comprising:
    the holder according to claim 9,
    one or a plurality of light-transmitting probes for emitting light towards said subject;
    one or a plurality of light-receiving probes for receiving light diffused and absorbed from said subject; and
    a control unit for acquiring measurement data on the brain activity of said subject by controlling said light-transmitting probes and said light-receiving probes.

* * * * *